(12) United States Patent
Barlev et al.

(10) Patent No.: US 6,917,183 B2
(45) Date of Patent: Jul. 12, 2005

(54) BATTERY PACK FOR STERILE TRANSFER BATTERY CONTAINER

(75) Inventors: B. Alex Barlev, Largo, FL (US); Eric N. Stubkjaer, Seminole, FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 10/137,519

(22) Filed: May 1, 2002

(65) Prior Publication Data

US 2003/0205987 A1 Nov. 6, 2003

(51) Int. Cl.[7] .................................................. H02J 7/00
(52) U.S. Cl. ........................... 320/112; 320/113; 429/1
(58) Field of Search ................................. 320/112, 107, 320/113, 110, 125, 104; 429/1, 59, 97, 98, 99, 100, 94, 159; 439/500

(56) References Cited

U.S. PATENT DOCUMENTS

| | | | | |
|---|---|---|---|---|
| 3,219,485 A | * | 11/1965 | Foecking et al. | 429/99 |
| 4,554,221 A | * | 11/1985 | Schmid | 429/1 |
| 5,187,422 A | * | 2/1993 | Izenbaard et al. | 320/110 |
| 6,265,091 B1 | * | 7/2001 | Pierson et al. | 429/1 |

* cited by examiner

Primary Examiner—Donald Sparks
Assistant Examiner—Lawrence Luk
(74) Attorney, Agent, or Firm—Gene Warzecha

(57) ABSTRACT

A rechargeable battery pack for a surgical powered instrument. The battery pack is an assembly of individual cylindrical battery cells and has its electrical terminals in the form of sockets recessed within the body of the pack in the interstices between the cells. The terminal sockets are adapted to receive elongated plugs and enable the pack to be handled while minimizing the risk of shorting.

1 Claim, 4 Drawing Sheets

BATTERY PACK FOR STERILE TRANSFER BATTERY CONTAINER

BACKGROUND OF THE INVENTION

1. Field of the Invention

The invention generally relates to battery operated surgical powered instruments. More particularly, the invention relates to battery packs which enable the use of non-sterile rechargeable batteries with sterile surgical instruments.

2. Description of the Prior Art

In order to enable the use of rechargeable non-sterile batteries in sterile surgical instruments, users employ a known "sterile transfer" technique. While possibly known by other names, this technique generally entails the sterilization and use of a sterile battery container to be attached to a sterile powered instrument. The sterilized container is held in a sterile field (by a scrub nurse, for example) and is shielded by a sterile shroud. A non-sterile, charged battery (held by a circulating nurse, for example) is placed into the sterilized container with care so as not to contaminate the already sterilized container. The shroud is then removed by the circulating nurse and the sterilized container is closed by the scrub nurse and attached to the instrument. The container hermetically encloses the battery and has its own exterior terminals which are connected to the battery terminals and through which the instrument is powered.

The battery used in a sterile transfer container is generally a battery pack comprising a plurality of individual battery cells wired and bound together in one unit. The terminals of the cells are connected in series and to the terminals of the battery pack. As used herein, the term "battery" will be understood to include a battery pack.

Prior art battery packs generally have terminal contacts which are surface mounted and engageable by contiguous engagement with another surface contact in the device with which the battery pack is designed to operate. The surface contacts are designed to be pressed toward each other, essentially pushing in opposite directions along an imaginary line passing through both contacts at the point at which they are contiguous. Sometimes a spring force is designed into the engagement to enhance the force with which the terminal contacts press against the device contacts.

Surface contacts are subject to vibration in powered surgical instruments and this may increase wear and affect performance. Also, surface contacts may subject a battery to risk of shorting if the battery terminals inadvertently connect conductive materials before being put into the intended instrument.

Additionally, surface contacts necessarily increase the size of the battery and/or battery/instrument combination. This occurs simply because of the necessity of providing relatively massive contacts and/or spring mechanisms to maintain a secure connection during use.

Accordingly, it is an object of this invention to produce a battery pack with increased security from failure.

It is also an object of this invention to produce a battery pack having a reduced risk of shorting across its terminals.

It is an additional object of this invention to produce a battery pack which has a smaller height to minimize the size of the sterile transfer container or instrument into which the battery pack is designed to fit.

SUMMARY OF THE INVENTION

These and other objects of this invention are achieved by the preferred embodiment disclosed herein which is a battery pack comprising a plurality of individual battery cells assembled into a predetermined configuration having interstices between the individual calls. Electrically positive and negative socket means are inserted into selected ones of the interstices, each socket means is adapted to mateably engage a plug. In one aspect of the invention the individual battery cells are cylindrical and the axes of the cells are all aligned with each other. The socket means may comprise a pair of leaf spring contact members adapted to receive therebetween a plug.

In another aspect the invention comprises a method of producing a battery pack in such away as to use the interstices between cylindrical cells to house electrical contacts. The method comprises the steps of assembling a plurality of cylindrical battery cells so that their respective axes are aligned and their cylindrical surfaces are contiguous to thereby form at least two parallel channels between predetermined ones of the cells. The method further comprises using each of the two parallel channels to receive therein respective positive and negative electrical contacts, wiring the electrical contacts to the battery cells to form a battery pack and securing battery cells together to form the battery pack.

DESCRIPTION OF THE PREFERRED EMBODIMENT

Figure 1:
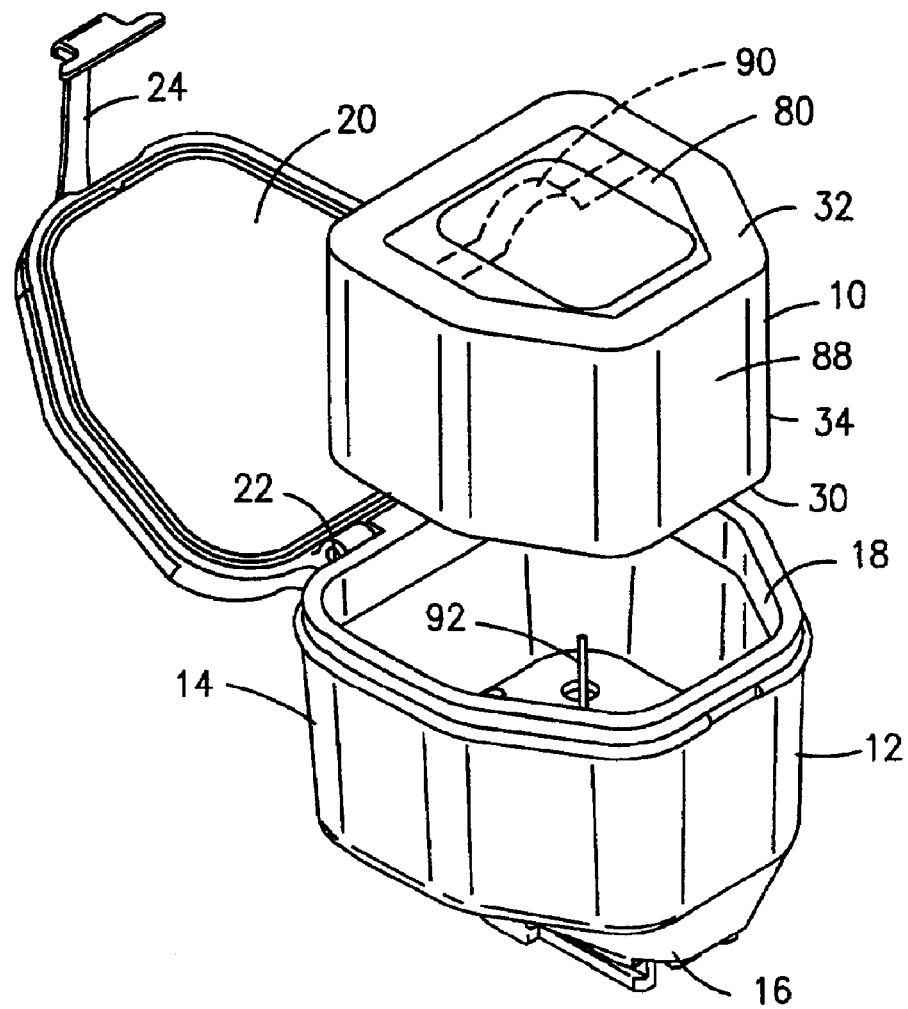
FIG. 1 is a bottom perspective view of an assembled battery pack, constructed in accordance with the principles of this invention, as it relates to a sterile transfer container designed to receive the battery pack.

Referring to FIG. 1, battery pack 10 is designed to fit in sterile transfer container 12. Container 12 has a hollow body 14 with a closed distal (top) end 16, and open proximal (bottom) end 18. The container is designed to be closed with cover 20, hinged at 22, and locked by locking mechanism 24. Details regarding sterile transfer container 12 are described in co-pending U.S. patent application entitled Sterile Transfer Battery Container assigned to the assignee hereof and incorporated by reference herein. Battery pack 10 has top and bottom surfaces 30 and 32, respectively, and has a peripheral wall surface 34.

Figure 4:
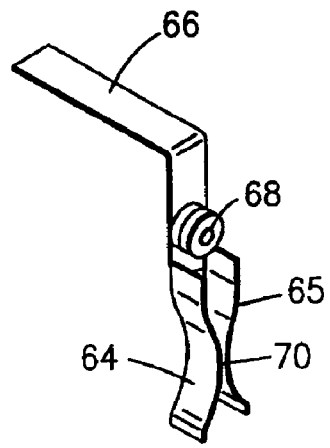
FIG. 4 is an exploded view of a portion of FIG. 3.
Figure 5:
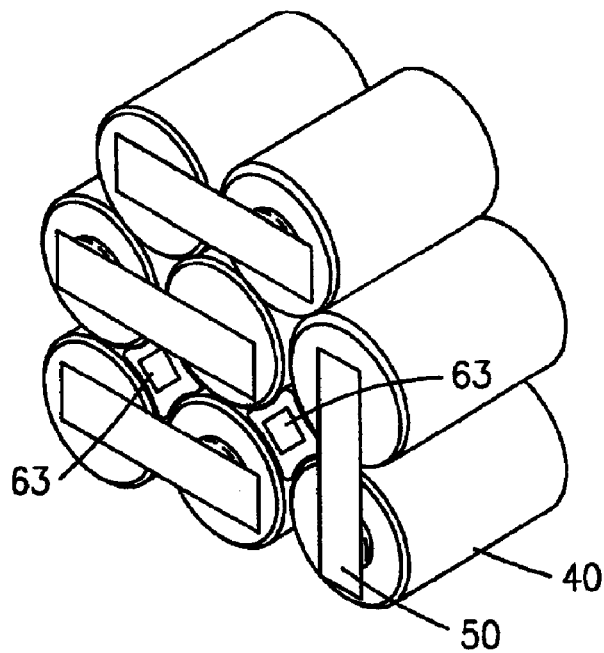
FIG. 5 is a top perspective view of a battery pack at another stage of its assembly.
Figure 6:
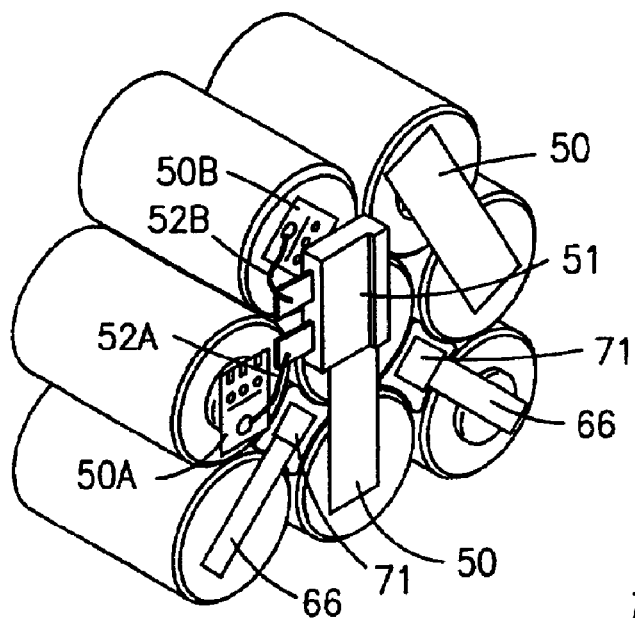
FIG. 6 is a bottom perspective view of a battery pack at another stage of its assembly.

As best seen in FIGS. 2 through 6, battery pack 10 is made up of a plurality of individual rechargeable battery cells 40. Each cell is in the form of a cylinder which has an axis 42, a cylindrical wall 44 and opposing positive and negative electrical terminals 46 and 48. The cells 40 are arranged in a conventional manner with their axes 42 aligned, their cylindrical walls 44 in contiguity and their electrical terminals alternating on adjacent cells. The alternation of the terminals facilitates wiring the cells in series by connecting straps 50, spot welded end tabs 50A and 50B, and fuse 51 in a conventional manner, as best seen in FIGS. 5 and 6. Wires 52A and 52B connect the fuse 51 in series between tabs 50A and 50B spot-welded to the bottoms of adjacent batteries. In prior art battery packs of this type the terminals of the individual cells are connected to surface mounted electrical terminals (not shown) secured to some exterior surface of the battery pack. As will be understood below, the invention disclosed herein utilizes unique and novel electrical terminals.

While cells 40 may be arranged in a cluster in a variety of ways to conform to the devices with which battery pack 10 is to be used, in the preferred embodiment the cells are arranged as shown in the drawings in three parallel rows A, B and C. Rows A and B have three cells each, side by side, and row C has two, nested adjacent the cells of row B and not side by side. The axes of the cells in rows A and B are arranged in a rectangular pattern. Each cell may be, for example, a nickel cadmium or nickel metal hydride rechargeable cell with a rating of 1.2 volts per cell, producing an eight cell battery pack with a rating of 9.6 volts. Other ratings could be produced with a different number of cells or different types (lithium ion, etc.).

Figure 2:
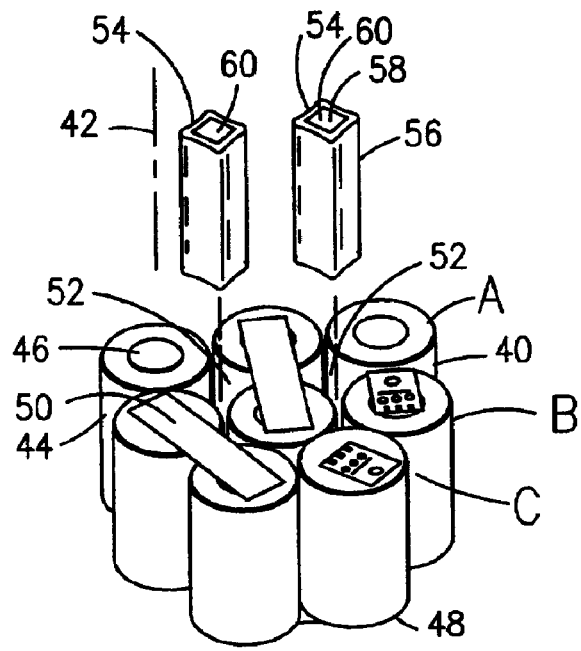
FIG. 2 is a top perspective view of the battery pack of FIG. 1 showing the battery pack partially assembled.
Figure 3:
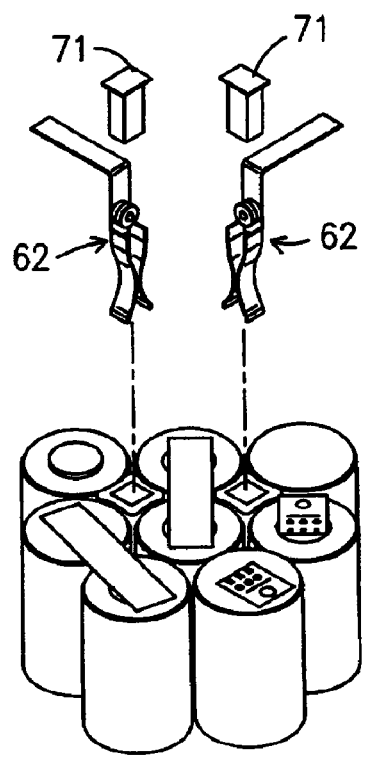
FIG. 3 is a view of FIG. 2 at a different stage in the assembly of the battery pack.

Referring to FIG. 2, it will be noted that the contiguous arrangement of cells in parallel rows, side by side, makes the cylindrical walls 44 create channels 52 between any four adjacent cells in rows A and B with their axes arranged at the corners of a square. Each channel is as long as the length of the individual cells and its cross-section is generally in the shape of a square having inwardly curved sides. Each channel is fitted with an electrically insulated, hollow electrode sleeve or retainer 54 having an exterior surface 56 conforming to its respective channel 52 and an interior surface 58. Electrode retainers 54 are inserted into channels 52 and retained by frictional engagement with cylindrical walls 44. In the preferred embodiment, interior surface 58 has a square cross-section and encloses a cavity 60 within each retainer 54. Each cavity 60 is adapted to receive, by frictional engagement preferably, an electrically conductive terminal contact 62 to thereby create an electrical socket 63. Each contact 62 has a pair of opposed leaf spring members 64 and 65, and a support member 66, all riveted together by rivet 68. Leaf spring members 64 and 65 are assembled as shown in FIG. 4 so that their opposed curvatures create a central point or gap 70 at which members 64 and 65 are either in contact or very close to each other. Support member 66 is used to connect leaf spring members 64, 65 to the terminals of two individual cells as best seen in FIG. 6. Reinforcing plugs 71 are inserted into the bottom of each retainer 54 and may be held in place by frictional engagement with the interior surface 58, by adhesive or by other suitable means. As explained below, plugs 71 keep contacts 62 from being pushed out of retainers 54 when a plug is engaged with socket 63.

FIGS. 5 and 6 show top and bottom perspective views, respectively, of a completely wired battery pack. At this stage of the assembly only minor additional steps are necessary to complete the fabrication of battery pack 10 to the final state shown in FIGS. 1 and 7. A plastic or other insulating end plate or covering 80 is used to cover the bottom of the cell assembly seen in FIG. 6. End plate 80 has, on its inner surface, one or more recesses (not shown) to receive and protect fuse 51 and other components. A similar plastic or other insulating end plate 82 is used to cover the top of the cell assembly seen in FIG. 5. End plate 82 has two apertures 84 and 86 to allow plug access to positive and negative sockets 63. The cell assembly shown in FIGS. 5 and 6, and the end plates 80 and 82 are then wrapped in an outer covering 88. In the preferred embodiment covering 88 is shrink-wrap material. A handle 90 of flexible cloth or other material may be secured to the bottom 32 of the battery pack to facilitate its removal from container 12.

It will be understood that elongated (flat or round) positive and negative plug members, such as plug member 92 seen in FIG. 1, can be inserted into the point/gap 70 through the open socket end 63 of each cavity 60, thereby establishing an electrical connection between the plug member 92 and the recessed contact 62. Only one plug 92 is seen in FIG. 1, but it will be understood that another plug is present. Similar plugs can be used on battery chargers or other devices with which battery pack 10 is to be connected.

Figure 7:
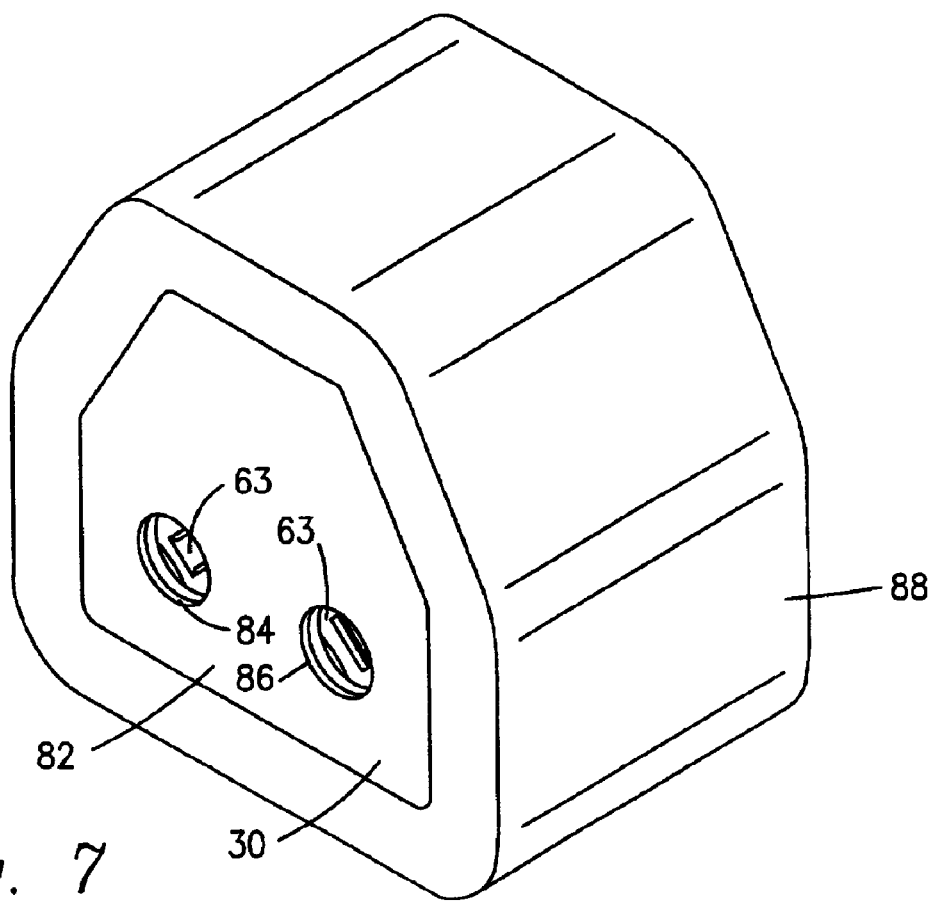
FIG. 7 is a bottom perspective view of a fully assembled battery pack.

As best seen in FIG. 7, because of the recessed configuration of the electrical contacts 62, battery pack 10 has a smooth, unobstructed bottom surface 30 which enables it to be placed on a metal surface or elsewhere without risking shorting the battery pack. Battery packs having different numbers of cells or cells arranged in different ways may produce channels of different cross-sections. However, retainers 54 may be produced in other cross-sections and contacts 62 may be produced in other shapes so that the principles of this invention may be applied to any other battery cell configuration. Basically, the interstices of the cell assembly are used to accommodate electrical sockets.

While this invention is explained herein in the context of a battery pack for use with sterile transfer techniques, it should be understood that the invention may be adapted to other techniques or devices. With appropriate modifications, the invention may be used in all situations suitable for conventional batteries.

It will be understood by those skilled in the art that numerous improvements and modifications may be made to the preferred embodiment of the invention disclosed herein without departing from the spirit and scope thereof.

What is claimed is:

1. A battery pack comprising:

a plurality of cylindrical battery cells assembled into a predetermined configuration wherein the axes of said cells are all aligned with each other, said configuration having interstices between the individual cells, said interstices comprising elongated channels; and electrically positive and negative socket means inserted into selected ones or said interstices, each sock means adapted to fit within selected channels and adapted to mateably engage a plug, each said socket means comprising a pair of opposed, elongated leaf spring contact members having a substantial point contact therebetween and adapted to receive therebetween an elongated plug; and a hollow, elongated retaining member adapted to be received within each said channel and adapted to retain said leaf spring contact members within said retaining member, each said hollow, elongated retaining member having a proximal end, defining an opening for receiving a plug, and an open distal end, further comprising a retaining plug adapted to prevent motion of said leaf spring contact members out of said open distal end; and securing means to secure said contact members from movement relative to said channel.

* * * * *